United States Patent
Chen et al.

(10) Patent No.: US 11,202,596 B2
(45) Date of Patent: Dec. 21, 2021

(54) SYSTEM AND METHODS FOR CONTROLLING NERVE ACTIVITY USING ELECTRICAL STIMULATION

(71) Applicant: Indiana University Research and Technology Corporation, Indianapolis, IN (US)

(72) Inventors: Peng-Sheng Chen, Indianapolis, IN (US); Lan S. Chen, Indianapolis, IN (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 108 days.

(21) Appl. No.: 16/479,094

(22) PCT Filed: Jan. 17, 2018

(86) PCT No.: PCT/US2018/013951
§ 371 (c)(1),
(2) Date: Jul. 18, 2019

(87) PCT Pub. No.: WO2018/136454
PCT Pub. Date: Jul. 26, 2018

(65) Prior Publication Data
US 2019/0374121 A1    Dec. 12, 2019

Related U.S. Application Data
(60) Provisional application No. 62/448,068, filed on Jan. 19, 2017.

(51) Int. Cl.
*A61B 5/24* (2021.01)
*A61B 5/00* (2006.01)
(Continued)

(52) U.S. Cl.
CPC .............. *A61B 5/24* (2021.01); *A61B 5/4035* (2013.01); *A61B 5/4836* (2013.01);
(Continued)

(58) Field of Classification Search
CPC . A61B 5/04001; A61B 5/4035; A61B 5/4836; A61B 5/4041; A61B 5/725;
(Continued)

(56) References Cited

U.S. PATENT DOCUMENTS

2006/0259077 A1* 11/2006 Pardo ................. A61N 1/36053
607/2
2009/0143831 A1    6/2009 Huston et al.
(Continued)

FOREIGN PATENT DOCUMENTS

WO    2014/035966 A1    3/2014
WO    2016064843 A1    4/2016

OTHER PUBLICATIONS

European search opinion dated Apr. 17, 2020 for EP Application No. 18741763.
(Continued)

*Primary Examiner* — Aaron F Roane
(74) *Attorney, Agent, or Firm* — Faegre Drinker Biddle & Reath LLP

(57) ABSTRACT

A system and methods utilizing electrical stimulation to achieve a desired therapeutic effect are provided. In one aspect, a method for controlling nerve activity in a subject is provided. The method includes receiving input indicating a desired therapeutic effect for at least one neural structure of a subject, and selecting, based on the input received, an electrical stimulation configured to achieve the desired therapeutic effect. The method also includes controlling a sympathetic nerve activity in the subject by delivering the
(Continued)

electrical stimulation using electrodes positioned proximate to nerves innervating the subject's skin.

9 Claims, 6 Drawing Sheets

(51) Int. Cl.
  *A61N 1/04* (2006.01)
  *A61N 1/36* (2006.01)
  *A61N 1/05* (2006.01)

(52) U.S. Cl.
  CPC .......... *A61N 1/0456* (2013.01); *A61B 5/4041* (2013.01); *A61B 5/725* (2013.01); *A61N 1/0476* (2013.01); *A61N 1/0551* (2013.01); *A61N 1/36031* (2017.08); *A61N 1/36034* (2017.08); *A61N 1/36057* (2013.01); *A61N 1/36114* (2013.01)

(58) Field of Classification Search
  CPC .............. A61N 1/0456; A61N 1/36031; A61N 1/36034; A61N 1/0476; A61N 1/0551; A61N 1/36057; A61N 1/36114
  USPC ............................................................ 607/2
  See application file for complete search history.

(56) References Cited

U.S. PATENT DOCUMENTS

| | | |
|---|---|---|
| 2012/0029601 A1 | 2/2012 | Simon et al. |
| 2012/0035680 A1 | 2/2012 | Napadow |
| 2013/0131743 A1* | 5/2013 | Yamasaki ............ A61N 1/3605 607/3 |
| 2014/0081355 A1 | 3/2014 | Marsh et al. |
| 2014/0155956 A1* | 6/2014 | Pless .................. A61N 1/36171 607/59 |
| 2015/0265830 A1* | 9/2015 | Simon ................ A61N 1/36034 600/13 |

OTHER PUBLICATIONS

IPEA/409—International Preliminary Report on Patentability dated Aug. 1, 2019 for WO Application No. PCT/US18/013951.
Supplementary European search report dated Apr. 17, 2020 for EP Application No. 18741763.
International Search Report and Written Opinion issued by the ISA/US Commissioner for Patents, dated Mar. 9, 2018, for International Application No. PCT/US2018/013951.

* cited by examiner

SYSTEM AND METHODS FOR CONTROLLING NERVE ACTIVITY USING ELECTRICAL STIMULATION

CROSS-REFERENCE TO RELATED APPLICATIONS

The present application is a U.S. national stage under 35 U.S.C. § 371 of International Application No. PCT/US2018/013951, filed on Jan. 17, 2018, which claims the benefit of and priority to U.S. Provisional Application No. 62/448,068, filed on Jan. 19, 2017, and entitled "SYSTEM AND METHODS FOR CONTROLLING NERVE ACTIVITY USING ELECTRICAL STIMULATION," the entire disclosures of which are expressly incorporated herein by reference in their entireties.

GOVERNMENT RIGHTS

This invention was made with government support under HL071140 and TR002208 awarded by the National Institutes of Health. The government has certain rights in the invention.

BACKGROUND

The present disclosure relates generally to systems and methods for controlling nerve activity and, in particular, to systems and methods for non-invasive controlling nerve activity using electrical stimulation.

Many diagnostic and treatment methods in the fields of medicine and biology rely on measurements of nerve activity in patients and test subjects. Nerve activity in humans and other animals generates electrical signals that are detectable by electronic equipment such as oscilloscopes and other electrical signal processing devices. In order to detect the nerve activity, one or more electrical conductors, or electrodes, are placed in proximity to the nerves being measured. The electrodes may receive the electrical signals for further medical analysis. In addition, various medical treatment methods also use electrodes to deliver electrical signals to the nerves in order to induce a response in the patient.

Cardiac care is one particular area of medical treatment that heavily utilizes measurement of nerve activity. Activity in the autonomic nervous system controls heart rate and blood pressure variability. The sympathetic and parasympathetic branches of the autonomic nervous system modulate cardiac activity. Elevated levels of sympathetic nerve activity ("SNA") are known to be correlated with heart failure, coronary artery disease, and may be associated with the initiation of hypertension. SNA is also thought to be important as a predictor of heart rhythm disorders, including sudden cardiac death.

Sympathetic nerve activity measurements have many medical uses including identification of specific conditions or determination of a treatment course. For example, previous studies have shown that directly recorded stellate ganglion nerve activity ("SGNA") immediately precedes heart rate acceleration and spontaneous cardiac arrhythmias. In general, sympathetic nerve activity is measured by bringing one or more electrodes into contact with a target nerve that is insulated from the surrounding tissue, and then the grouped action potentials are measured. Notwithstanding that measured signals are typically in the microvolt range, variations in contact between the nerves and electrodes can produce inconsistencies in the recorded signals. In addition, access to the target nerves generally involves invasive procedures. For example, direct recording of SGNA would necessitate an incision into the pleural space of the chest.

Cardiac sympathetic innervation derives from the paravertebral cervical and thoracic ganglia. In particular, the stellate (cervicothoracic) ganglion is a major source of cardiac sympathetic innervation, formed by the fusion of the inferior cervical ganglion and the first thoracic ganglion. Clinical studies have shown that the stellate ganglion is an important component in cardiac arrhythmogenesis, with excessive sympathetic outflow believed to be a major cause of heart rhythm problems. Hence, reducing the sympathetic outflow of the stellate ganglion, via resection or ablation, is generally recognized to help prevent sudden death in patients with life threatening ventricular arrhythmias. However, such techniques necessitate invasive procedures that have prevented their widespread use, particularly for patients with less than lethal cardiac arrhythmias, due to the risks and complications involved.

Therefore, there is a continuing need for systems and methods for addressing various cardiac and other conditions.

SUMMARY

The present disclosure overcomes the drawbacks of previous technologies by introducing a system and methods to control nerve activity of a subject using electrical stimulation. Specifically, a novel approach is introduced whereby the activity or structure of targeted neural structures can be modified using electrical stimulation to achieve a desired therapeutic effect.

In one aspect of the present disclosure, a method for controlling nerve activity in a subject is provided. The method includes receiving input indicating a desired therapeutic effect for at least one neural structure of a subject, and selecting, based on the input received, an electrical stimulation configured to achieve the desired therapeutic effect. The method also includes controlling a sympathetic nerve activity in the subject by delivering the electrical stimulation using electrodes positioned proximate to nerves innervating the subject.

In another aspect of the present disclosure, a method for treating a subject using electrical stimulation is provided. The method includes receiving input indicating a desired therapeutic effect a subject and generating, based on the input received, an electrical stimulation configured to achieve the desired therapeutic effect. The method also includes delivering the electrical stimulation using electrodes positioned proximate to nerves innervating the subject.

In yet another aspect of the present disclosure, a method for producing a report indicating an electrical stimulation for achieving a desired therapeutic effect is provided. The method includes sampling electrical signals from a subject and applying a filter to the electrical signals to generate filtered signals. The method also includes identifying a nerve activity using the filtered signals, and estimating a sympathetic nerve activity using the identified nerve activity. The method further includes generating an electrical stimulation configured to achieve a desired therapeutic effect based on the sympathetic nerve activity, and producing a report indicating the electrical stimulation.

In yet another aspect of the present disclosure, a system for controlling nerve activity in a subject is provided. The system includes a plurality of electrodes configured to engage a subject and deliver electrical signals thereto, and a signal generator, in communication with the plurality of electrodes, configured to provide the electrical signals. The system also includes a processor programmed to execute instructions stored in a non-transitory computer readable medium select an electrical stimulation configured to achieve a desired therapeutic effect for at least one neural structure accessible using the subject, and control a sympathetic nerve activity in the subject by directing the signal generator to deliver the electrical stimulation using plurality of electrodes.

The foregoing and other advantages of the invention will appear from the following description.

DETAILED DESCRIPTION

Figure 1:
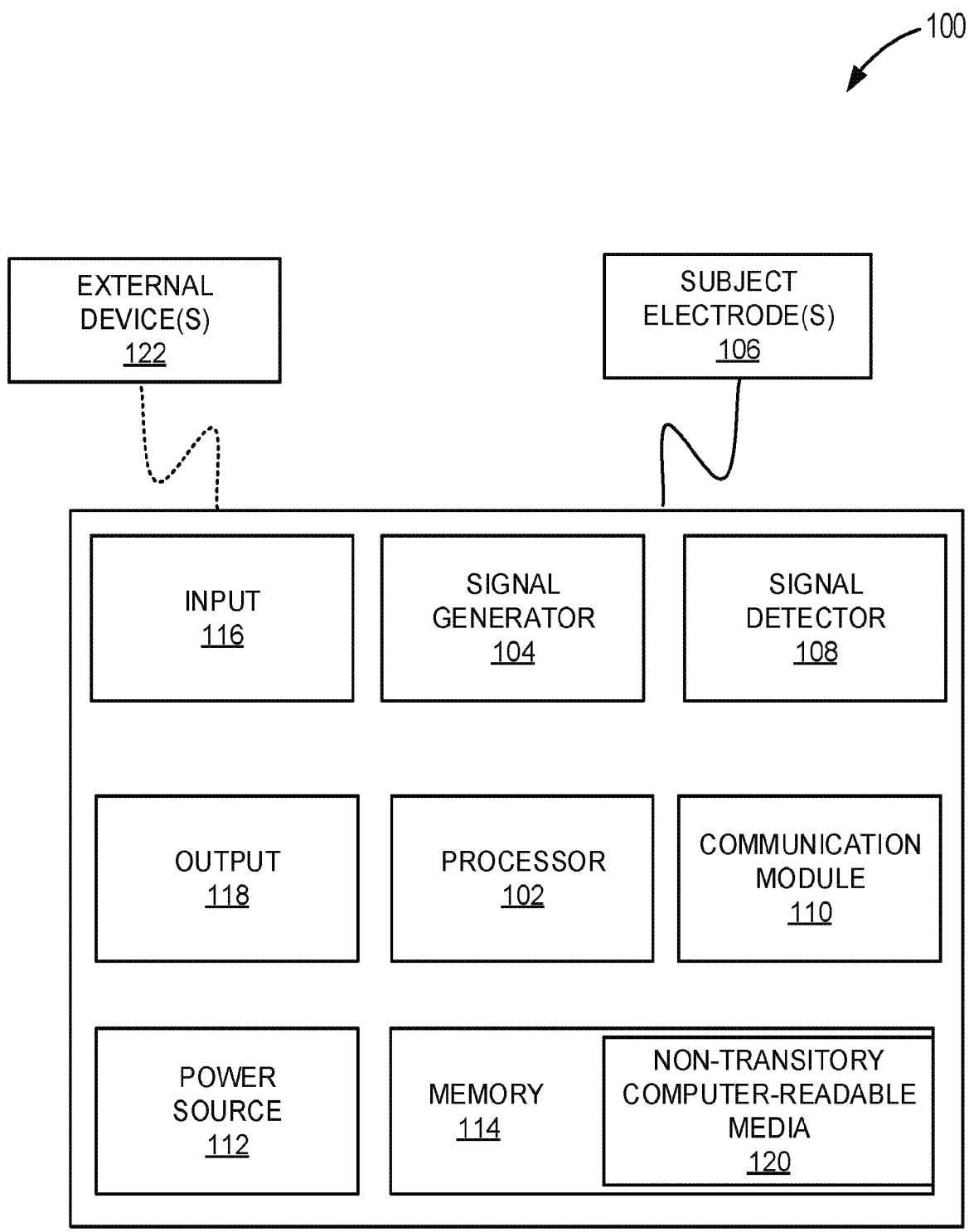
FIG. 1 a schematic diagram of an example system for monitoring and/or controlling nerve activity of a subject, in accordance with aspects of the present disclosure.

Excessive sympathetic outflow from the stellate ganglion is believed to be a major cause of heart rhythm problems, and may partly account for the pathophysiology of heart failure. Traditional treatments for managing heart rhythm have relied on medications. Others have utilized surgical removal or ablation of the stellate ganglion. More recently, it was recently discovered by the inventors that stimulating the vagal nerve can induce stellate ganglion remodeling and decrease in sympathetic nerve activity. Such decrease can provide therapeutic effects, such as controlling ventricular rate during atrial fibrillation. However, the vagal nerve is an anatomical structure that is critical to many bodily functions. As a result, vagal nerve stimulation procedures carry a significant risk and require a high degree of technical expertise. In addition, the need for accessing the vagal nerve often limits practical clinical usage. Therefore, safer and less invasive techniques are required.

Therefore, the present disclosure introduces a novel approach for use in treating various medical conditions. Specifically, a system and methods are herein provided that utilize electrical stimulation to achieve a desired therapeutic effect. In accordance with aspects of the present disclosure, electrical stimulation of nerves innervating a subject may be used to remodel targeted neural structures, such as the stellate ganglion and others. Electrical stimulation using the skin is non-invasive, or minimally invasive, and can help control nerve activity that often leads to various heart and other medical problems. In addition, such approach significantly reduce potential risks and complications associated with more invasive procedures, and advance clinical translation.

In some aspects, nerve activity measurements may be used to determine a treatment involving electrical stimulation, in accordance with a desired therapeutic effect. For instance, sympathetic nerve activity can be obtained by measuring skin nerve activity ("SKNA"). That is, electrical signals acquired using cutaneous and/or subcutaneous electrodes, placed at various locations about a subject's skin, may be used to estimate sympathetic nerve activity, such as stellate ganglion nerve activity ("SGNA"). In this manner, information useful in the diagnosis as well as treatment of various medical conditions, such as heart rhythm problems, may be generated without need for invasive and more risky procedures. For instance, information associated with SGNA, and other nerve activities of a subject, may be used to predict cardiac arrhythmia, as well as provide a risk stratification. In addition, such information may be useful in determining electrical stimulation parameters or treatment course.

The description below and the accompanying figures provide a general understanding of the environment for system and methods disclosed herein as well as the details for the system and methods. In the drawings, like reference numerals are used throughout to designate like elements.

As used herein, the term "electrode" refers to any electrical conductor that is configured to sense electrical signals from a subject, such as biological tissue, when coupled to or brought into contact with the subject.

As used herein, the terms "proximity" and "proximate" when used to describe the location of an electrode with respect to the skin of a test subject mean that the electrode is placed in a location on the surface (epidermis) of the skin or under the skin near the hypodermis to enable the electrode to receive electrical signals corresponding to nerves that innervate the skin. For example, in a cutaneous configuration, the electrode is placed in contact with a surface of the skin of the test subject, with some embodiments using an electrical conductor such as a conductive gel to promote electrical contact between the electrode and the skin. In a subcutaneous configuration, the electrode is implanted under the skin of the test subject to enable the electrodes to receive electrical signals in nerves that innervate the hypodermis. In a subcutaneous configuration, the electrode is either in contact with the hypodermis or located within a short distance from the hypodermis, such as under a layer of adipose tissue that is under the skin.

As used herein, the term "cutaneous" as applied to use of electrodes refers to placing electrodes on the surface of the skin of a subject without puncturing the skin of the subject. As described below, the cutaneous electrodes detect electrical activity associated with nerves that are proximate to the skin of the subject, including sympathetic nerves in the autonomic nervous system that innervate the skin.

As used herein, the term "subcutaneous" as applied to use of electrodes refers to placing electrodes entirely underneath the skin with leads from the electrodes being electrically connected to a device that is placed in the body of the test subject, such as an internal pacemaker, defibrillator, or cardiac resynchronization device. The subcutaneous electrodes described herein are different than electrodes that are used in prior art microneurography procedures. First, the subcutaneous electrodes are completely under the skin, with no portion of the electrode or lead extending through the skin. Second, the subcutaneous electrodes do not have to be placed in close proximity to a particular nerve fiber to be used in detection of electrical signals from nerve activity. Third, the subcutaneous electrodes are shaped with a blunt contact surface without the sharp needle tips of microneurographic electrodes, which enables the subcutaneous electrodes to remain under the skin of an ambulatory subject for long term monitoring of nerve activity without injuring the subject. Fourth, the metal housing of an implanted device can be used to house subcutaneous electrodes in some embodiments. In the latter situation, no additional electrodes are needed.

In both the cutaneous and subcutaneous configurations described above, the electrodes are located proximate to nerves that innervate the skin. As is known in the medical art, many nerves that innervate the skin are part of the sympathetic nervous system, which is in turn part of the autonomic nervous system in humans and many animals. Different nerve fibers in the sympathetic nervous system also innervate cardiac tissue as well as other muscles and organs in the body. For example, the sympathetic nervous system is associated with the "fight or flight" response where the sympathetic nervous system activity increases and the pupils dilate, the heart rate increases, bronchioles in the lungs dilate, blood vessels near the surface of the skin constrict, and the sweat glands secrete sweat at a higher rate. The sympathetic nervous system is also associated with the "sympathetic outflow" process that occurs when a subject awakens from sleep. While the sympathetic nervous system includes a large number of nerve bundles that innervate different parts of the body in a subject, the nerves in the sympathetic nervous system are associated with each other and the level of activity in one nerve fiber often corresponds to the level of activity in other nerve fibers in the sympathetic nervous system.

As used herein, the term "therapeutic effect" may generally refer to any effect or change in a subject's condition, modifiable directly or indirectly using electrical stimulation. In one non-limiting example, a therapeutic effect may include a change in sympathetic nerve activity. In another non-limiting example, a therapeutic effect may include a change sympathetic tone of one or more neural structures. In another non-limiting example, a therapeutic effect may include a remodeling of one or more neural structures. In yet another non-limiting example, a therapeutic effect may include a change in the functionality or function of one or more cells, tissues, structures or organs in the subject. In yet another non-limiting example, a therapeutic effect may include a change in arrhythmia, heart rhythm or heart rate. In yet another non-limiting example, a therapeutic effect may include a change in nerve density or level of enervation.

As used herein, the term "arrhythmia" refers to any abnormal activity in the heart of a subject. Examples of arrhythmia include, but are not limited to, tachycardia, bradycardia, atrial flutter, atrial fibrillation, premature contractions, ventricular fibrillation, heart palpitations, and cardiac arrest.

As used herein, the term "remodel" used in relation to one or more neural structures may refer to a change in the structure, size, composition or functionality of the neural structure(s) or various constituents therein.

As used herein, terms such as "approximately," "around," "about," and other synonyms, in relation to stated numerical values may include variations as understood by one of ordinary skill in the art. In some aspects, such variation may be negative (less than a nominal value) or positive (more than a nominal value), and up to 100%, or more, of the stated nominal value(s).

Turning to FIG. 1 a non-limiting example of a system 100, for use in diagnosing and treating various medical conditions, in accordance with aspects of the present invention, is shown. In some applications, the system 100 may be used to control a nerve activity in a subject.

In general, the system 100 may include a processor 102, a signal generator 104, and a plurality of electrodes 106. As shown in FIG. 1, the system 100 may also include a signal detector 108, a communication module 110, a power source 112, and a memory 114. The system 100 may further include an input 116 and an output 118. Any combination of these, and other, components may be included in a single or multiple housings.

The system 100 may be a stand-alone system, a wearable or portable device, such as a fully or partially implantable device, pacemaker, and so forth. In addition, the system 100 may operate autonomously or semi-autonomously using various information, such as data or instructions, provided via input 116 or exchanged with an external device(s) 122, as shown in FIG. 1. The system 100 may also have access to and process information stored in a database, a storage server, cloud, and other locations.

The processor 102 can include one or more microcontrollers, microprocessors, and other processing units, that are configured to perform a variety of processing steps to control the system 100. In addition to being designed or programmed to operate the system 100, the processor 102 may be configured to execute steps, in accordance with methods of the present disclosure. In some implementations, the processor 102, or processing unit therein, may execute non-transitory programming, or instructions hardwired therein. Such processor 102 or processing unit would therefore be application-specific. Alternatively, or additionally, the processor 102 may include a general-purpose processor configured to access and execute instructions stored in non-transitory computer readable media 120 of the memory 114. In some implementations, the processor 102 may alternatively, or additionally, execute steps based on input from a user providing operational instructions or selections, for example. However, user input is not required as the system 100 and processor 102 may be configured to operate in an open-loop mode.

In one example, the processor 102 may include a central processing unit ("CPU") with one or more cores, and optionally a graphical processing unit ("GPU"). The processor 102 may also include one or more digital logic devices, including application specific integrated circuits ("ASICs"), field programmable gate arrays ("FPGAs"), and digital signal processor ("DSP") devices. In addition, in some portable or implantable device embodiments of the system 100, the processor 102 may also include low-power digital logic devices that enable long-term operation between battery recharge or replacement.

In accordance with aspects of the present disclosure, the processor 102 may be configured to control nerve activity, such as SGNA, to achieve a desired therapeutic effect. As detailed below, the processor 102 may direct the signal generator 104 to generate and deliver to targeted tissues and neural structures, such as nerves, plexi and other structures, a treatment protocol that includes electrical stimulations. In some aspects, the processor 102 may select a treatment protocol to achieve a desired therapeutic effect. In other aspects, the processor 102 may select a treatment protocol based on various measurements or estimations. For instance, the processor 102 may direct the signal detector 108 to sample electrical signals from the subject corresponding to nerve activities, such as SKNA or SGNA. In some aspects, various signal processing functions may be performed on sampled electrical signals, including filtering, scaling, digitizing, and so on. By way of non-limiting example, executable software for signal processing tasks in processor 102 may include the PowerLab data acquisition software commercially available from ADInstruments of Sydney, Australia. The processor 102 may then carry out various internal calculations and determine an appropriate treatment protocol based on a desired therapeutic effect. In determining and selecting the treatment protocol, the processor 102 may utilize input, measurements, and other information, along with a database having stored therein various tabulated information. For example, the database may data correlating treatment protocols, or stimulation parameters, and various therapeutic effects, and other factors.

The signal generator 104 may include various hardware and circuitry for generating electrical stimulation signals, as directed by the processor 102, including various voltage and current sources, and circuit elements. The signal generator 104 may be configured to provide electrical stimulation signals that are continuous or intermittent, to be delivered using one or more electrodes 106 coupled to the subject, as will be described. In turn, the electrodes 106 may be arranged in any number of lead configurations, and positions on the subject's anatomy. In some implementations, the electrodes 106 are configured to engage the subject's skin cutaneously and/or subcutaneously. In addition, one or more of the electrodes 106 may also be configured to measure various physiological signals from the subject. In particular, such electrodes 106 may be coupled or electrically connected to specific tissues or structures, such as cutaneous or subcutaneous nerves, or proximate to such tissues or structures, to enable effective detection of electrical signals. In some arrangements, electrodes 106 may be arranged to facilitate monitoring of both nerve activity and cardiac activity. The electrodes 106 may also be configured or include sensors for measuring other physiological signals, including heart rate, respiration, and so forth.

As described, the system 100 also includes a signal detector 108 configured to acquire various electrical signals from the subject. In some implementations, the signal detector 108 may include amplifiers capable of amplifying voltage signals, or differential voltage signals, received from the electrodes 106. The signal detector 108 may also include samplers or sampling circuitry that can generate digitized samples of amplified signals via an analog to digital converter ("ADC") for further processing by the processor 102. By way of example, the signal amplifier(s) and sampler(s) may be configured to amplify signals in a frequency range of approximately 1 Hz to 5,000 Hz and to generate digital samples of the amplified signals at a rate of 10,000 samples per second. In one example embodiment, the signal amplifier(s) and sampler(s) may include an ML 135 dual-bio amplifier that is manufactured by the ADInstruments of Sydney, Australia. In some aspects, the signal amplifier(s) and sampler(s) may be electrically connected to the electrodes 106 in a configuration that includes at least one reference electrode and two input signal electrodes.

The communication module 110 may be configured to facilitate communications between the system 100 and one or more external device(s) 122. In particular, the communication module 110 may be capable of facilitating data and information exchange with the external device(s) 122, and other hardware, via wired or wireless communication. The communication module 110 may include any hardware, software, firmware, and in some aspects be capable of telemetry, Bluetooth or other wireless communication protocol. In some implementations, the communication module 110 may also be configured to receive user input, such as operational instructions, as well as provide various information, in any form, related to operational parameters, signals detected and/or processed, such as cardiac activity, nerve activity, and the like. Alternatively, such instructions may be provided via the input 116, which can include buttons, touchscreens, keyboard, mouse, and other input elements. The communication module 110 may also be configured to provide information or a report regarding delivered electrical stimulations or measured/processed electrical signals. Additionally, or alternatively, such information or report may be provided via output 118, which may include monitors, indicators, LCD displays, speakers, and the like.

The memory 114 may include various memory elements where a number of types of data (e.g., internal data, external data instructions, software codes, status data, diagnostic data, etc.) may be stored. In addition, as shown in FIG. 1, the memory 114 may also include non-transitory computer-readable media 120, which may include instructions executable by the processor 102 for operating the system 100 as well as carrying out methods in accordance with present disclosure. Example elements in the memory 114 may include random access memory ("RAM"), dynamic random access memory ("DRAM"), electrically erasable programmable read-only memory ("EEPROM"), flash memory, and the like. The memory 114 may also include various information, including various treatment protocols tabulated based on desired therapeutic effects. The memory 114 may also include various correlations between sympathetic nerve activity, including stellate ganglion activity, and skin nerve activity. Such correlations may be stored as waveforms, series, tables or other data representations.

Referring again to FIG. 1, based on the subject condition and desired therapeutic effect, the processor 102 may select an appropriate treatment protocol, autonomously or semi-autonomously. The processor 102 may then direct the signal generator 104 to deliver the treatment protocol via electrodes 106. The treatment protocol may include intermittent or continuous stimulation. Specifically, intermittent stimulation includes periods of electrical stimulation, or "ON" periods, and periods of non-stimulation, or "OFF" periods. The number, duration, and temporal arrangement of "ON" and "OFF" periods in an intermittent stimulation may vary. In some aspects, the "ON" and "OFF" periods may be unequal in duration and, in this regard, the treatment may be referred to as asynchronous. For example, a treatment protocol may include brief "ON" periods, approximately 1 to 20 seconds in duration, separated by long "OFF" periods, for example, lasting approximately 60 seconds to 15 minutes in duration, although other values may be possible. Electrical stimulation during any "ON" period may be in the form of current pulses delivered at frequencies approximately between 0.1 Hz and 30 Hz, or more, with pulse widths approximately between 0.1 milliseconds and 5 milliseconds and intensities up to approximately 5 milliAmperes (mA). Other stimulation parameter values may be possible, and the form of the electrical stimulation may vary. For example, an electrical stimulation during an "ON" period may be sinusoidal, or another waveform, and may also be provided as voltage.

In some aspects, the processor 102 may select a treatment protocol based on user input. Such input may be indicative of targeted tissues or neural structures, as well as desired therapeutic effect for the targeted tissues or neural structures. By way of example, a desired therapeutic effect may include remodeling one or more neural structures, decreasing or increasing the level of enervation of tissues or organs, or affecting nerve activity or tone produced. To this end, electrical stimulation parameters in the treatment protocol may be adapted based on the desired therapeutic effect. For instance, it is a discovery of the present disclosure, as will be described, that electrical stimulation using cutaneous and/or subcutaneous electrodes and current pulses with intensities above approximately 1.0 mA can reduce stellate ganglion activity, and sympathetic tone, by causing stellate ganglion tissue remodeling or damage. By contrast, current pulses with intensities below approximately 1.0 mA can produce nerve proliferation, or nerve sprouting, in the stellate ganglion, hence increasing stellate ganglion activity, and sympathetic tone.

In some aspects, the processor 102 may additionally, or alternatively, select or adapt the treatment protocol using information obtained from monitored nerve activities or changes thereof. For instance, the treatment protocol may be customized by taking into consideration a baseline neural activity, such as a sympathetic or parasympathetic nerve activity, or a nerve activity, and a target neural activity or target ventricular rate. Additionally, the treatment protocol may be adapted based on a change in nerve activity or condition as a result of prior treatment or other event.

In some aspects, the processor 102 of system 100 may perform a number of signal processing steps to identify nerve activity in data samples received from the signal detector 108. Specifically, the processor 102 may be configured to estimate a sympathetic nerve activity, such as stellate ganglion activity, based on identified nerve activity, for example, using determined correlations stored in the memory 114.

As described in more detail below, the electrical activity in the nerves that innervate the skin occurs at higher frequencies and lower amplitudes compared to the electrical signals generated in the cardiac muscle during a heartbeat. As such, processor 102 may be configured to identify and monitor the electrical signals corresponding to specific signals in the subject, such as nerve or cardiac activity, by processing data samples received from the signal detector 108. That is, the processor 102 may apply appropriate filters, such as low-pass filters, high-pass filters, or band-pass filters, to the data to obtain signals of interest. The processor 102 may also scale, multiply or integrate various measured signals.

For example, a 3 dB high-pass filter lower with a cutoff frequency adjustable in a range of approximately 100-1 kHz may be utilized. Selection of the proper high-pass setting might require consideration of signal specificity and acceptable sensitivity. For instance, a high-pass cutoff frequency of 150 Hz would be sufficient to attenuate most the lower frequency signals from cardiac muscle activity and electrical signals from other muscles in the subject typically observed, but not all muscle noise. On the other hand, a cutoff at 700 Hz would be more specific to nerve activity, as the muscle noise does not generate signals with frequencies above 500 Hz, but such filter setting would result in a reduced measurement sensitivity. In some preferred embodiments, the high-pass filter cutoff frequency may be between 150 Hz and 700 Hz, although other values may be possible.

In some aspects, data samples may also be processed using a low-pass filter, for example, with a cutoff frequency approximately in a range between 10 Hz and 150 Hz in order to detect cardiac activity. Alternatively, a band-pass filter may be applied to monitor the ECG of the subject using the amplified signal samples from the signal detector 104. For example, the band-pass filter may have a lower cutoff frequency of approximately 0.5 Hz and an upper cutoff frequency of approximately 100 Hz. In some implementations, the same pair of electrodes 106 (e.g. patch electrodes) may be used to simultaneously record electrocardiogram ("ECG") and skin nerve activity from the surface of thoracic skin, for example. In such case, the same signals may be used to determine both ECG and SKNA. Specifically, the signals may be low-pass filtered (selective ECG signals) and high-pass filtered (selective for SKNA). Additionally, where an alternating current ("AC") electrical signal is used to supply power to one or more components in system 100, a band-pass filter also includes a notch-filter that attenuates frequencies near the primary frequency of the AC signal, such as 50 Hz or 60 Hz.

In addition to monitoring electrical signals corresponding to nerve activity and optionally the ECG activity, the processor 102 may also be configured to analyze such activity and take an appropriate action in response. For example, the processor 102 may identify a baseline nerve activity, such as a skin or sympathetic nerve activity, and changes in nerve activity relative to the baseline as determined, for instance, using average signal amplitude or signal variation.

Cardiac events are not the only types of medical events that relate to the nerve activity in the sympathetic nervous system. For instance, nerve activity can be indicative of hyperhidrosis (sweaty palms), paralysis, stroke, diabetes, seizure disorder, syncope, disturbance of consciousness, hyperthyroidism, hypertension and neuromuscular diseases. Therefore, it is envisioned that the system 100 described herein may be advantageously used in many of these applications.

In one example, the system 100 may be used identify a suitability for receiving an electrical stimulation therapy to treat certain medical conditions, such as hypertension and cardiac arrhythmia. In another example, the system may be used for neuromodulation therapy, such as renal sympathetic denervation, to reduce or modify sympathetic nerve activity. In yet another example, the system 100 may be used to monitor nerve activity to provide guidance while performing a procedure, and also to determine an effectiveness of a treatment, ascertained using changes in nerve activity. Another area of application of the present system 100 includes monitoring nerve activity during lie-detection tests. This is because sympathetic nerve activation is the mechanism that regulates sweating, pupil contraction, and other physiological responses that are measured during lie detector tests. Thus, the system 100 may be used to identify changes in the nerve activity of the subject. Yet other areas of application include biofeedback monitoring performed by neurologists to control neuropsychiatric disorders.

Figure 2:
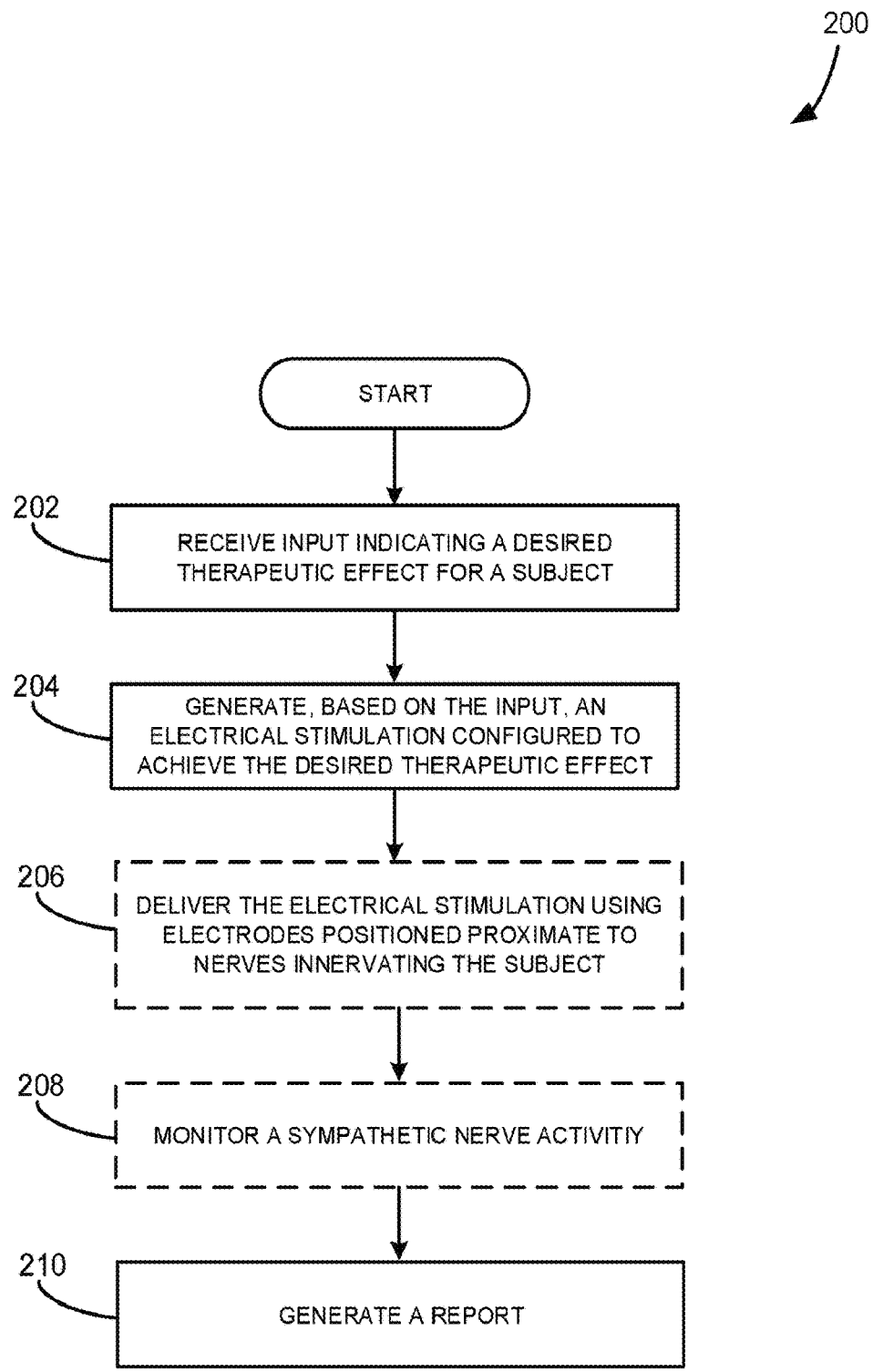
FIG. 2 shows steps of a process, in accordance with aspects of the present disclosure.

Turning now to FIG. 2, the steps of a process 200, in accordance with aspects of the present disclosure, are shown. In some implementations, the process 200 may be used to control nerve activity. In another implementations, the process 200 may be used to generate a report indicating an electrical stimulation for achieving a desired therapeutic effect, such as controlling nerve activity. The process 200 may be carried using a system 100, as described with reference to FIG. 1, or another suitable system, device or apparatus. Steps of the process 200 may be implemented as a program, firmware, or executable instructions hardwired or stored in non-transitory computer readable media.

The process 200 may begin at process block 202 with receiving input indicating a desired therapeutic effect. As described, desired therapeutic effects may include controlling a sympathetic nerve activity, remodeling targeted neural structures, charging levels of innervation of a tissue or organ, such as the stellate ganglion, affecting or treating a medical condition of the subject, such as cardiac arrhythmia, and so on. To this end, the input may be indicative of targeted tissues, organs or neural structures, as well as desired therapeutic effect for the targeted tissues or neural structures. The input may also be indicative of the method or configuration of electrical stimulation. For instance, the input may be indicative of the number and position of electrodes, as well as whether cutaneous and/or subcutaneous electrodes are used. The input may also be indicative of subject characteristics, such as age, gender, height, weight, and so on, as well as information related to the subject, such as medical conditions, baseline nerve activities (e.g. sympathetic nerve activity, skin nerve activity, and so on), prior treatments, and so forth.

Then, at process block 204, an electrical stimulation configured to achieve the desired therapeutic effect may be generated based on the input received. This step may include selecting specific stimulation parameters and/or a treatment protocol. The selection may include accessing a memory, database, or other information storage location, having therein tabulated data and information. For example, an accessed database may include various data correlating therapeutic effects with stimulation parameters or treatment protocols for achieving those therapeutic effects.

In some aspects, a selected treatment protocol may include a number of "ON" and "OFF" periods of various durations. For example, a treatment protocol may include brief "ON" periods of electrical stimulation, each lasting approximately 1 to 20 seconds, separated by long "OFF" periods, for example, approximately 60 seconds to 15 minutes in duration, although other values may be possible. In addition, electrical stimulation during any "ON" period may include current pulses delivered at frequencies approximately between 0.1 Hz and 30 Hz, with pulse widths approximately between 0.1 milliseconds and 5 milliseconds, and intensities up to approximately 5 milliAmperes (mA). It may be appreciated that other stimulation parameters and protocols may be possible, depending upon targeted structures or tissues, and desired therapeutic effects. For example, electrical stimulation during any "ON" period may be sinusoidal, or another waveform. Furthermore, electrical stimulation may alternatively be provided as voltage. In addition, for some desired therapeutic effects, the intensity of electrical stimulation may be adjusted gradually over a period of time, such as over several hours, days, or weeks.

As described herein, it is a discovery of the present disclosure that controlling sympathetic tone may depend upon the specific stimulation parameters selected. For instance, current pulses with intensity above approximately 1.0 mA may be used to induce stellate ganglion damage, and thereby reduce corresponding sympathetic tone and/or stellate ganglion activity. By contrast, current pulses with intensities below approximately 1.0 mA can produce nerve proliferation or nerve sprouting (increased innervation) in the stellate ganglion, and thereby increase corresponding sympathetic tone or stellate ganglion activity. Therefore, selecting stimulation parameters at process block 204 may take into consideration various predetermined thresholds for producing the desired therapeutic effects. In the example above, a predetermined threshold differentiating stellate ganglion damage from nerve proliferation to control sympathetic tone may be approximately 1.0 mA.

Then, at process block 206, the selected electrical stimulation may be optionally delivered to achieve the desired therapeutic effect. In some aspects, the electrical stimulation may be delivered using electrodes positioned proximate to nerves innervating a target area of the subject, such as the skin, such as using cutaneous and/or subcutaneous electrode.

In some implementations, a sympathetic nerve activity may be optionally monitored during, or following, the delivered electrical stimulation, as indicated by process block 208. For example, a stellate ganglion nerve activity or a skin nerve activity may be monitored. In addition, various physiological signals may also be monitored at process block 208. For example, a cardiac signal, a blood pressure signal, a respiratory signal, and others may also be monitored. Monitoring nerve activity and physiological signals may help determine an effectiveness of the electrical stimulation, as well as ensure safety of the subject. Effectiveness of the electrical stimulation may be determined, for instance, by analyzing changes of a sympathetic nerve activity or skin nerve activity as compared to a baseline. In some aspects, monitored nerve activities may be used to estimate a sympathetic nerve activity. Effectiveness of the electrical stimulation may be determined from other indicators or events, such as the occurrence of arrhythmia.

A report may then be generated at process block 210. The report may be provided in substantially real time, for example, using a display, or stored in a memory to be retrieved at a later time. The report may indicate a user input, as well as a generated or delivered electrical stimulation, or a progress thereof. In some aspects, the report may be in the form of graphs or time traces of monitored or estimated nerve activity. Displayed or retrieved activities corresponding to monitored or estimated nerve activities may then utilized by a doctor or other healthcare professional during or following the course of medical treatment for a subject. The report may also include information derived from measurements or estimations of nerve activity, including average signals, signal variations, signal frequencies, frequency variations, identified events, event timings, deviations from a baseline, and so forth.

Figure 3:
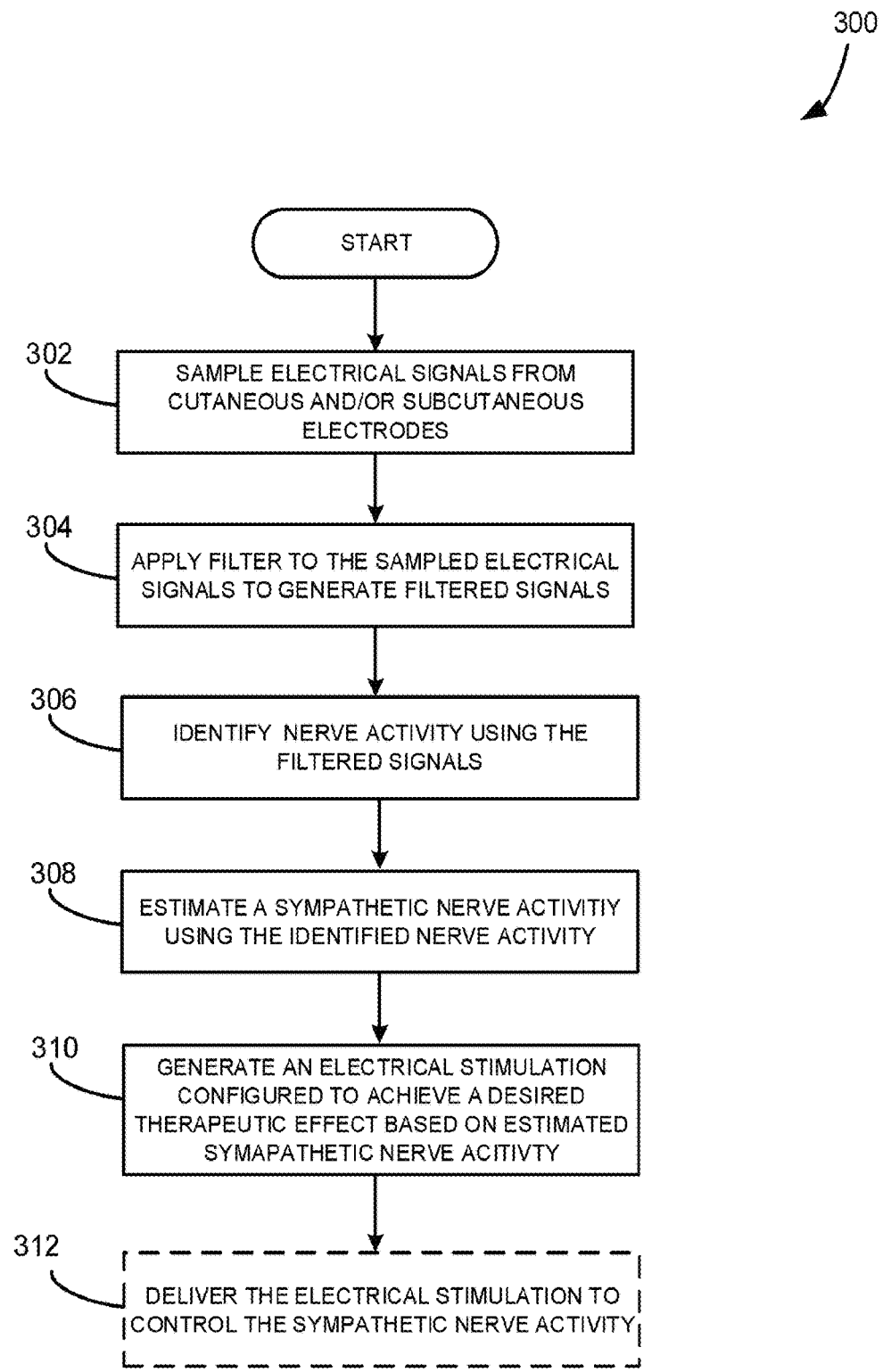
FIG. 3 shows steps of another process, in accordance with aspects of the present disclosure.

Referring now to FIG. 3, steps of a process 300, in accordance with aspects of the present disclosure, are shown. In some implementations, the process 300 may be used to control nerve activity. In another implementations, the process 300 may be used to generate a report indicating an electrical stimulation for achieving a desired therapeutic effect. The process 300 may be carried using a system 100, as described with reference to FIG. 1, or another suitable system, device or apparatus. Steps of the process 300 may be implemented as a program, firmware, or executable instructions hardwired or stored in non-transitory computer readable media.

The process 300 may begin at process block 302 with sampling electrical signals using cutaneous and/or subcutaneous electrodes coupled to a subject. In some configurations, three or more electrodes, may be placed on the subject in a cutaneous configuration. Electrodes may be additionally, or alternatively implanted under the skin of the subject in a subcutaneous configuration, although other arrangements are possible.

In order to effectively deliver therapeutic effects, selection of electrode locations might take into consideration enervations of skin at potential locations, and the strength of electrical coupling between skin nerves therein and targeted neural structures. For example, electrodes may be placed at skin locations about the thorax of a subject, or more specifically at or above the $5^{th}$ thoracic space. In particular, this location is associated with connections between skin sympathetic nerves and the stellate ganglion. Other locations, depending upon the targeted neural structure, or tissue, may also be possible. In some aspects, the sampled electrical signals may be include amplified differential voltage signals that are received from the electrodes and generate digitized samples of the signals.

Process 300 may then continue with application of a filter to the sampled electrical signals to generate filtered signals, as indicated by process block 304. In some aspects, the filter may be configured to attenuate at least signals having frequencies that correspond to heart muscle activity during a heartbeat. Other signal filtering, as well as processing steps may also be possible at process block 304, including scaling, multiplying, or integrating the signals sampled at process block 302. In some aspects, a high-pass filter may be applied to the processed signal samples. Specifically, the high-pass filter may have a lower cutoff frequency in a range of 100 Hz to 1 kHz in order to attenuate lower-frequency electrical signals that correspond to cardiac activity in the subject instead of the nerve activity. The lower-frequency cutoff of the high-pass filter can be adjusted based on the characteristics of different subjects to enable identification of the electrical signals in the nerves that innervate the skin while attenuating the electrical signals from muscles and other sources of electrical noise in the subject. For example, the high-pass filter may have a cutoff frequency of approximately 700 Hz. Thus, at process block 306, a skin activity may be identified using high-frequency signals that pass through the high-pass filter.

At process block 308, a sympathetic nerve activity may then be estimated using the identified skin nerve activity. For instance, predetermined correlations or relationships between skin nerve activity and a stellate ganglion nerve activity may be utilized to determine the estimates. Such correlations may be stored in a memory or database, for example. Using the estimated sympathetic nerve activity, an electrical stimulation configured to achieve a desired therapeutic effect may be generated, as indicated by process block 310. In some aspects, the generated electrical stimulation may also be based on a user input, which is indicative of the desired therapeutic effect, as described.

The electrical stimulation may then be optionally delivered to control the sympathetic nerve activity, as indicated by process block 312. In some aspects, changes to the sympathetic nerve activity may be monitored during or following the electrical stimulation. Alternatively, a report indicative of the electrical stimulation generated at process block 310 may be generated and provided at process block 312. The report may include a variety of information. For instance, the report may indicate stimulation parameters and/or treatment protocol for achieving the desired therapeutic effect. The report may also include information for adapting a treatment.

In some implementations, methods described herein may be carried out in a passive operating mode, displaying the nerve activity and recording nerve activity in the memory for subsequent retrieval and analysis by medical professionals. In such passive operating mode, therapeutic devices need not be activated automatically. That is, a doctor or other healthcare provider would retrieve and review information or data associated with acquired or estimated nerve activity as part of diagnosis and treatment in a subject. The passive operating mode can be used, for example, during diagnosis of a medical condition, during long-term monitoring of a subject to assess progress in a course of medical treatment, and for studies of subjects during clinical trials or other scientific research.

In other implementations, methods described herein may be carried out to generate a baseline measurement of nerve activity in a subject, such as stellate ganglion nerve activity baseline. For example, the baseline nerve activity can include an average signal amplitude, or signal variation. The baseline activity could then be used to determine a change in the level of nerve activity over time, for example, as a result of a change in medical condition, or as a result of treatment. A determined rapid change in the electrical signals corresponding to the sympathetic nerve activity that deviates from the baseline by more than a predetermined threshold, could then initiate an audio or visual alarm to a clinician in response to the identified change in nerve activity. In some aspects, a message, page, email, text message, or other report may be sent to alert a remote healthcare professional of the identified event.

The above-described system and methods may be further understood by way of examples. These examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims. For example, certain electrode arrangements and configurations are presented, although it may be understood that other configurations may be possible, and still considered to be well within the scope of the present invention. Likewise, specific process parameters and methods are recited that may be altered or varied based on variables such as signal amplitude, phase, frequency, duration, and so forth.

EXAMPLE I

The stellate ganglia ("SG") are major sources of thoracic sympathetic nerves. It was hypothesized that thoracic subcutaneous nerve stimulation (SCNS) can damage the SG, reduce SG nerve activity (SGNA) and control paroxysmal atrial tachycardia (PAT). Therefore, SCNS was performed at Xinshu acupoint (located on the back, below the spinous process of the 5th thoracic vertebra, roughly 5.5 cm lateral to the posterior midline) in 6 dogs and left lateral thoracic nerve (LLTN) in 2 dogs. The SGNA, vagal nerve activity (VNA) and subcutaneous nerve activity (SCNA) before and after the start of SCNS was monitored.

Figure 4A:
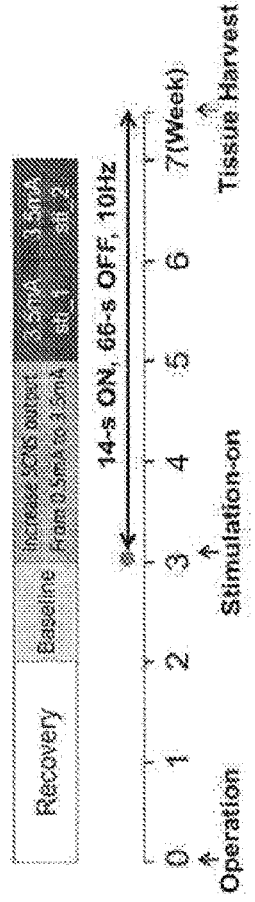
FIG. 4A is a schematic of an example treatment protocol for controlling nerve activity in a subject, in accordance with aspects of the present disclosure.
Figure 4B:
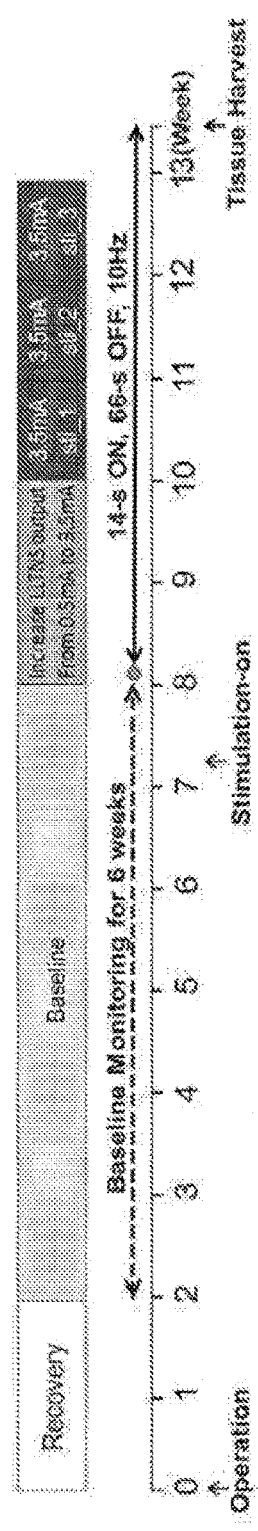
FIG. 4B is a schematic of another example treatment protocol for controlling nerve activity in a subject, in accordance with aspects of the present disclosure.

The protocol for Xinshu subcutaneous nerve stimulation (n=6) is shown in FIG. 4A. After baseline recording, neurostimulator was turned on (red dot) and programmed 14-s ON (10 Hz, 500 μs pulse duration) and 66-s OFF. The output current was increased gradually from 0.5 mA to 3.5 mA in 2 weeks. After an additional 2 weeks of stimulation, the dogs were euthanized. The protocol for the left lateral thoracic nerve stimulation (n=2) is shown in FIG. 4B. In comparison to the Xinshu point, the baseline recording was extended to 6 weeks. The neurostimulator was turned on at week 8 and the output was gradually increased to 3.5 mA over a 2 week period. After an additional 3 weeks of stimulation at 3.5 mA, the dogs were euthanized.

Figure 4C:
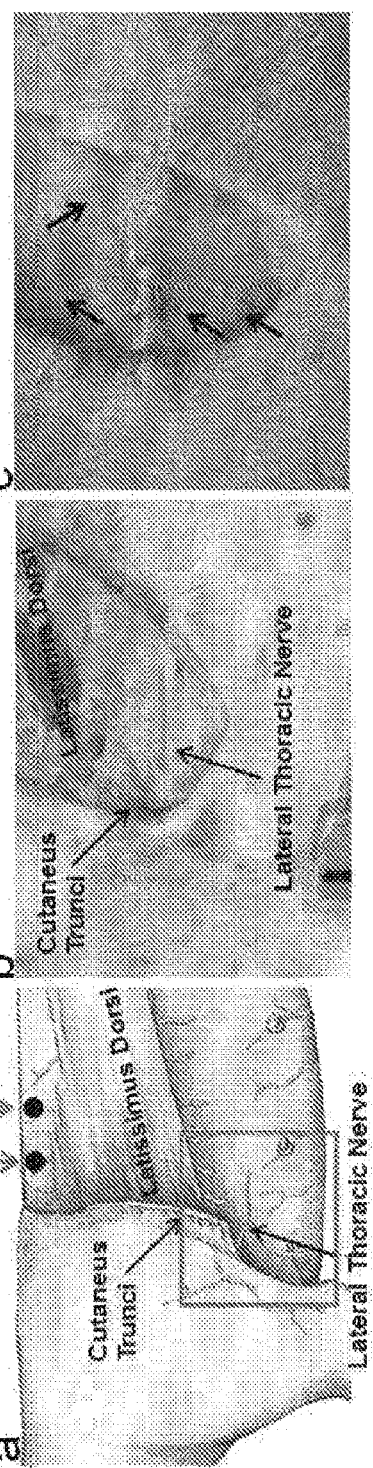
FIG. 4C are illustrations showing sites of electrical stimulation, in accordance with aspects of the present disclosure.

FIG. 4C (a) shows the sites of electrical stimulation. Red arrow indicates site of Xinshu acupoint while blue arrow points to cutaneous nerves of the dorsal branch of the thoracic nerve. FIG. 4C (b) is an image of an incision at the upper portion of the red box reveals LLTN beneath the cutaneus trunci. FIG. 4C (c) is an image showing the simulation wires wrapped around the LLTN. The black arrows point to subcutaneous nerves, which are also found at Xinshu acupoint. (SCNS=Xinshu subcutaneous nerve stimulation, LLTNS=left thoracic nerve stimulation, 3.5 mA sti_1, 3.5 mA sti_2 and 3.5 mA sti_3 are the first, second and third week of 3.5 mA stimulation, respectively).

Figure 5:
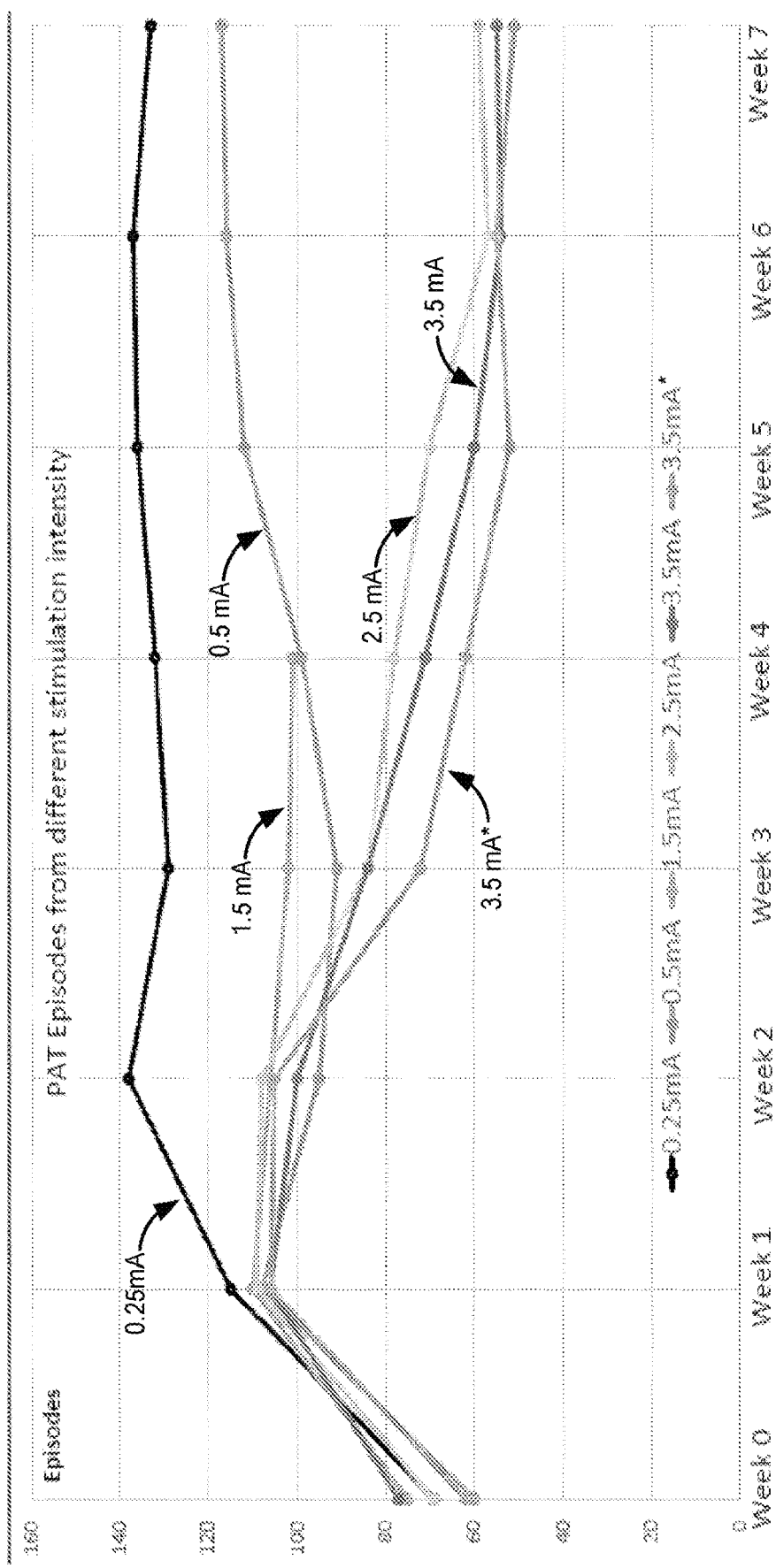
FIG. 5 is a graph comparing the effects of different stimulation intensities on paroxysmal atrial tachycardia ("PAT") episodes for animal subjects, in accordance with aspects of the present disclosure.

Results showed that SCNS and LLTN were both associated with reduced heart rate (HR). SCNS at 3.5 mA for 2 weeks reduced the mean integrated SGNA (iSGNA) from 1.78 mV-s [95% confidence interval, CI, 1.50 to 2.06] at baseline to 1.45 mV-s [95% CI, 1.16 to 1.75] (P=0.028) and the mean HR from 89 bpm [95% CI, 80 to 98] at baseline to 83 bpm [95% CI, 76 to 90] (P=0.007). Tyrosine hydroxylase (TH) staining of bilateral SG showed regions of neuronal injury (FIG. 5). The Terminal deoxynucleotidyl transferase dUTP nick end labeling (TUNEL) stain showed 18.47% [95% CI, −9.68 to 46.62] of all ganglion cells were TUNEL-positive (FIG. 5). PAT episodes reduced from 9.83 per day [95% CI, 5.77 to 13.89] at baseline to 3.00 [95% CI, 0.11 to 5.89] after SCNS (P=0.027). LLTN SCNS also significantly reduced iSGNA and HR in both dogs studied, that had significant bilateral SG damage. These results demonstrate that SCNS at two different sites in the thorax can damage the SG, reduce SGNA and suppress PAT in ambulatory dogs.

To identify whether a lower output produced similar results, additional studies on 6 dogs were also performed. The studies utilized a similar stimulation protocol applied to the Xinshu acupoint as described above, namely: 10 Hz, 14-seconds ON time and 66 seconds OFF time intermittent stimulation. The low output group including one dog at 0.25 mA and one at 0.5 mA. Cardiac rhythm monitoring studies showed increase number of paroxysmal atrial tachycardia ("PAT") episodes during follow up. The remaining 4 dogs stimulated at 1.5 mA, 2.5 mA, 3.5 mA and 3.5 mA. As shown in FIG. 5, for dogs stimulated above 2.5 mA, the PAT episodes were suppressed, while the dog that received 1.5 mA did not show appreciable effects on PAT episodes.

Figure 6:
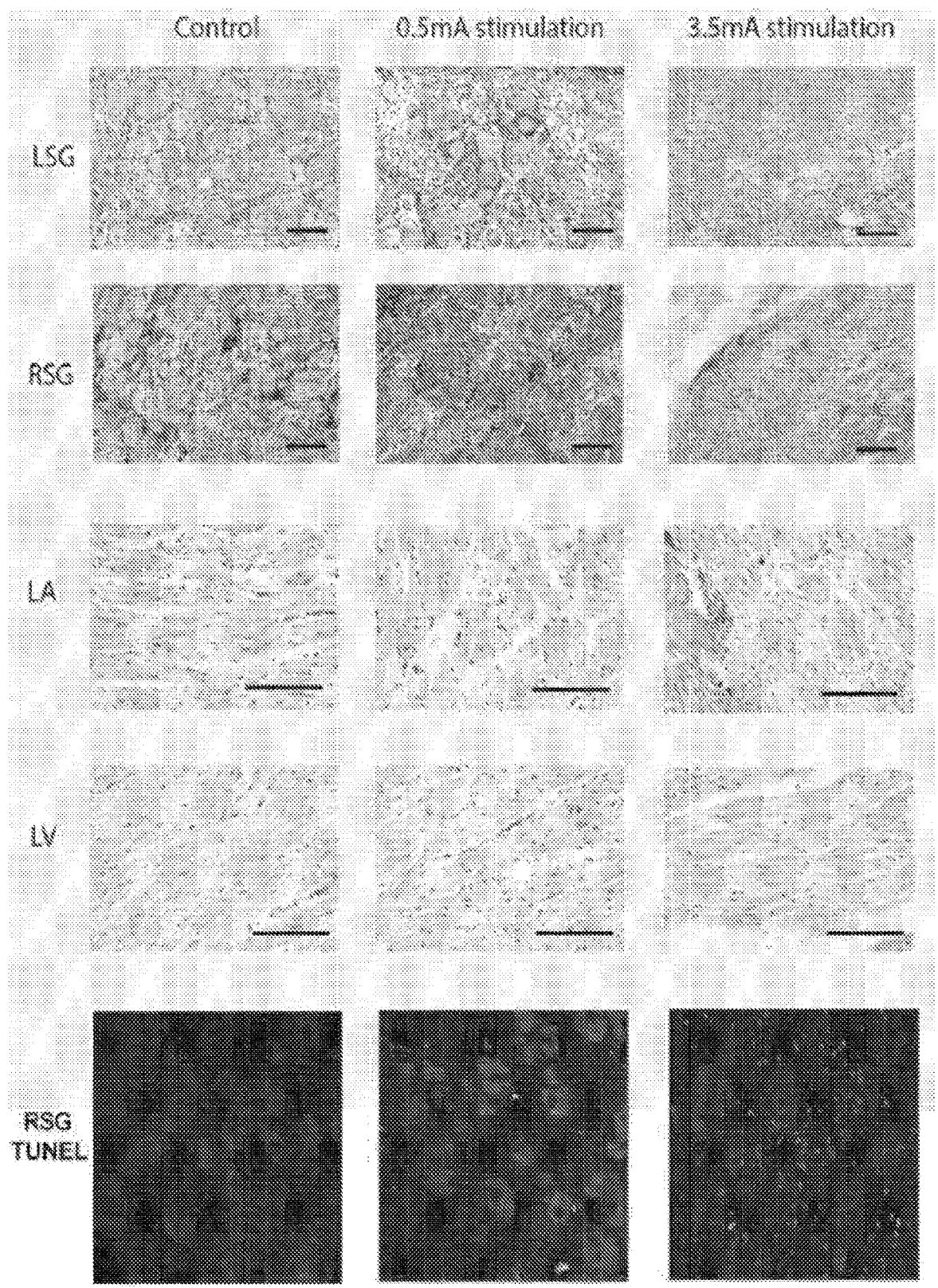
FIG. 6 show histological images comparing results from low and high current intensity stimulation relative to a control, in accordance with aspects of the present disclosure.

Histological studies were also performed, and the results are shown in FIG. 6. In particular, high output stimulation at 3.5 mA produced stellate ganglion damage in dogs. Control data is also shown for comparison. Low output stimulation resulted in nerve sprouting and sympathetic hyperinnervation. In particular, electrical current at 0.5 mA caused significantly increased staining of the growth associated protein 43 (GAP43) in the left and right stellate ganglia and in the left and right ventricles heart. The increased GAP43 staining indicates cardiac nerve sprouting, which increases sympathetic nerves. In contrast, 3.5 mA stimulation reduced the GAP43 staining. TUNEL staining (green color is positive) identifies the DNA fragmentation, which is characteristic of cell death. Only 3.5 mA stimulation showed signs of DNA fragmentation, and hence cell death in the SG.

In conclusion, it was found that low output stimulation to the thoracic subcutaneous nerves can cause cardiac and stellate ganglion nerve sprouting, sympathetic hyperinnervation and increased physiological consequences (i.e., increased number of PAT). In particular, stimulation at 0.25 mA or 0.5 mA can grow sympathetic nerves in the sympathetic ganglia and the organs innervated by that sympathetic ganglia in dogs. On the other hand, high output stimulation caused excitotoxicity and cell death. These findings indicate that the stimulus output is critical to the desired therapeutic effect.

The present discovery is significant and has wide range of applications in procedures involving electrical stimulations. Specifically, results herein suggest that SCNS may be used in others parts of the body to increase, as well as decrease, sympathetic enervation and sympathetic tone. For example, SCNS may be used to increase sympathetic nerves in the legs, and elsewhere. In addition, heart failure is known to cause increased circulating catecholamine and reduced innervation to the heart. The reduced innervation prevented appropriate uptake of the catecholamines from the heart, which may contribute to the pathophysiology of heart failure. SCNS with low output, in accordance with the present disclosure, might be used to grow nerves in the heart, and thus counteract the detrimental effects of denervation. Additionally, multiple other diseases outside the heart can cause denervation. For example, patients with spinal cord injury or diabetes are known to have reduced or ineffective innervation. The ability to grow nerves through low output subcutaneous stimulation may help those conditions.

EXAMPLE II

The various configurations presented above are merely examples and are in no way meant to limit the scope of this disclosure. Variations of the configurations described herein will be apparent to persons of ordinary skill in the art, such variations being within the intended scope of the present application. In particular, features from one or more of the above-described configurations may be selected to create alternative configurations comprised of a sub-combination of features that may not be explicitly described above. In addition, features from one or more of the above-described configurations may be selected and combined to create alternative configurations comprised of a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

The invention claimed is:

1. A method for treating a subject using electrical stimulation, the method comprising:
    receiving input indicating a desired therapeutic effect a subject, wherein the desired therapeutic effect comprises one or more of remodeling at least one neural structure of the subject to reduce a sympathetic nerve activity in the subject, remodeling at least one neural structure of the subject to increase a sympathetic nerve activity in the subject, or controlling a stellate ganglion nerve activity;
    generating, based on the input received, an electrical stimulation configured to achieve the desired therapeutic effect;
    delivering the electrical stimulation using electrodes positioned proximate to nerves that innervate the subject's skin and delivers intermittent current with an intensity above or below a predetermined threshold depending on the desired therapeutic effect and wherein the intermittent current is delivered in periods of stimulation lasting from 12 to 16 seconds and separated by time intervals lasting between 1 minute and 3 minutes and at an intensity below a predetermined threshold of 1.0 mA depending on the desired therapeutic effect.

2. The method of claim 1, wherein periods of stimulation comprise pulses with a pulse width of 0.5 milliseconds delivered at a frequency of 10 Hz.

3. The method of claim 1, wherein the method further comprises delivering the electrical stimulation using electrodes coupled to cutaneous nerves or subcutaneous nerves, or both.

4. A system for controlling nerve activity in a subject, the system comprising:
- a plurality of electrodes configured to engage a subject's skin and deliver electrical signals thereto;
- a signal generator, in communication with the plurality of electrodes, configured to provide the electrical signals; and
- a processor programmed to execute instructions stored in a non-transitory computer readable medium to:
  - provide an electrical stimulation configured to achieve a desired therapeutic effect for at least one neural structure accessible using the subject's skin, wherein the desired therapeutic effect comprises one or more of remodeling at least one neural structure of the subject to reduce a sympathetic nerve activity in the subject, remodeling at least one neural structure of the subject to increase a sympathetic nerve activity in the subject, or controlling a stellate ganglion nerve activity;
  - control a sympathetic nerve activity in the subject by directing the signal generator to deliver the electrical stimulation using the plurality of electrodes; and
  - wherein the processor is further configured to direct delivery of an intermittent current with an intensity above or below a predetermined threshold depending on the desired therapeutic effect and wherein the intermittent current is delivered in periods of stimulation lasting between 12 and 16 second and separated by time intervals lasting between 1 minute and 3 minutes; and
  - wherein the processor is further configured to direct delivery of the intermittent current with an intensity below a predetermined threshold of 1.0 mA depending on the desired therapeutic effect.

5. The system of claim 4, wherein the plurality of electrodes are configured to engage cutaneous nerves, subcutaneous nerves, or a combination thereof, in the subject's skin.

6. The system of claim 4, wherein periods of stimulation comprise pulses with a pulse width of 0.5 milliseconds delivered at a frequency of 10 Hz.

7. The system of claim 4, wherein the system further comprises a signal detector configured to acquire signals from the subject's skin.

8. The system of claim 7, wherein the processor is further configured to monitor the sympathetic nerve activity using the signals acquired from the subject's skin.

9. The system of claim 8, wherein the processor is further configured to determine a medical condition of the subject using the monitored sympathetic nerve activity.

\* \* \* \* \*